US008835383B2

(12) United States Patent
Ludwig et al.

(10) Patent No.: US 8,835,383 B2
(45) Date of Patent: Sep. 16, 2014

(54) METHOD FOR CONTROLLING THE DIGESTIVE COAGULATION OF PROTEINS

(75) Inventors: Thomas Ludwig, Wageningen (NL); Claudia Catharina Maria van den Braak, Wageningen (NL); Marianne Klebach, Wageningen (NL); Zandrie Hofman, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 13/266,409

(22) PCT Filed: Apr. 27, 2010

(86) PCT No.: PCT/NL2010/050241
§ 371 (c)(1),
(2), (4) Date: Jan. 6, 2012

(87) PCT Pub. No.: WO2010/131952
PCT Pub. Date: Nov. 18, 2010

(65) Prior Publication Data
US 2012/0094901 A1  Apr. 19, 2012

(30) Foreign Application Priority Data
Apr. 27, 2009  (NL) ................. PCT/NL2009/050227

(51) Int. Cl.
| A61K 38/02 | (2006.01) |
| A23J 3/10 | (2006.01) |
| A23J 3/16 | (2006.01) |
| A23J 3/14 | (2006.01) |
| A23L 1/305 | (2006.01) |
| A61K 36/48 | (2006.01) |
| A61K 38/01 | (2006.01) |
| A61K 38/16 | (2006.01) |
| A23L 1/29 | (2006.01) |

(52) U.S. Cl.
CPC ............. *A23L 1/296* (2013.01); *A23L 1/3055* (2013.01); *A23L 1/3056* (2013.01); *A61K 36/48* (2013.01); *A61K 38/018* (2013.01); *A61K 38/168* (2013.01); *A23V 2002/00* (2013.01)
USPC ............. 514/5.7; 530/378; 530/370; 530/360

(58) Field of Classification Search
CPC ... A61K 38/168; A61K 38/02; A61K 38/011; A61K 38/01; A61K 38/00; A23V 2002/00; A23V 2200/32; A23V 2200/30; A23V 2250/54252; A23V 2250/54246; A23V 2250/5424; A23V 2250/542; A23V 2250/55; A23V 2250/5488; A23V 2250/548; A23V 2250/54; A23V 2250/00
USPC .......................................................... 514/5.7
See application file for complete search history.

(56) References Cited

U.S. PATENT DOCUMENTS

| 5,021,245 | A | 6/1991 | Borschel et al. |
| 5,486,461 | A | 1/1996 | Nielsen |
| 5,547,927 | A | 8/1996 | Cope et al. |
| 5,635,199 | A | 6/1997 | Trimbo et al. |
| 6,355,297 | B1 | 3/2002 | Sawatzki et al. |
| 6,475,539 | B1 * | 11/2002 | DeWille et al. ................. 426/72 |
| 6,565,900 | B2 | 5/2003 | Roussel et al. |
| 8,097,262 | B2 | 1/2012 | Kuribayashi et al. |
| 8,618,047 | B2 | 12/2013 | Hofman et al. |
| 2001/0018066 | A1 | 8/2001 | Hahn |
| 2003/0104033 | A1 * | 6/2003 | Lai et al. ........................ 424/439 |
| 2006/0188643 | A1 | 8/2006 | Solorio et al. |
| 2008/0031860 | A1 | 2/2008 | Hageman |
| 2008/0226810 | A1 | 9/2008 | Passe et al. |
| 2010/0086668 | A1 | 4/2010 | Abrahamse et al. |
| 2010/0088252 | A1 | 4/2010 | Le-Henand et al. |
| 2012/0283180 | A1 | 11/2012 | Hofman et al. |
| 2012/0309831 | A1 | 12/2012 | Van Anholt et al. |

FOREIGN PATENT DOCUMENTS

| EP | 0 626 175 A2 | 11/1994 | |
| EP | 0 626 175 B1 | 11/1994 | |
| EP | 0 626 176 A2 | 11/1994 | |
| EP | 1 059 040 B1 | 9/2006 | |
| EP | 1 972 345 A1 | 9/2008 | |
| EP | 1 972 346 A1 | 9/2008 | |
| EP | 2 073 781 A2 | 7/2009 | |
| GB | 1 507 380 | 4/1978 | |
| WO | WO-93/19624 A1 | 10/1993 | |
| WO | WO-02/098242 A1 | 12/2002 | |
| WO | WO-2004/047549 A1 | 6/2004 | |
| WO | WO-2006/052134 A2 | 5/2006 | |
| WO | WO-2007/004883 A2 | 1/2007 | |
| WO | WO 2007/063142 | * 6/2007 | ............ A61K 38/16 |
| WO | WO/2008/032432 | * 3/2008 | ............ A61K 47/36 |
| WO | WO 2008/046857 | * 4/2008 | ............ A61K 45/06 |
| WO | WO-2008/046857 A1 | 4/2008 | |
| WO | WO-2008/046871 A2 | 4/2008 | |

(Continued)

OTHER PUBLICATIONS

U.S. Appl. No. 13/266,736, filed Oct. 2011, Hofman et. al.*
International Search Report for PCT/NL2009/050227, dated Jan. 25, 2010, 3 pages.
International Search Report for PCT/NL2010/050241, dated Jun. 29, 2010, 2 pages.
Meneses et al., "Evaluación biológica de la calidad de un mezcla de proteínas para uso en nutrición enteral", Nutr. Hosp., vol. 23, No. 3, Madrid, 2008, pp. 206-211. (Abstract).
Who Technical Report Series 935, "Protein and Amino Acid Requirements in Human Nutrition: Report of a Joint FAO/WHO/UNU Expert Consultation," 2007, p. 241-247, p. 245, and Table 49.
International Search Report for PCT/NL2011/050060 dated Mar. 16, 2011.
Abrahamsson, "Gastrointestinal motility disorders in patients with diabetes mellitus", Jounral of Internal Medicine, 1995, vol. 237, pgs. 403-409.

(Continued)

Primary Examiner — Karlheinz R Skowronek
Assistant Examiner — Catherine Mader
(74) Attorney, Agent, or Firm — Gilberto M. Villacorta; Sunit Talapatra; Foley & Lardner LLP

(57) ABSTRACT

This invention relates to the coagulation of protein containing nutritional compositions in the upper gastro-intestinal tract, more in particular in the stomach and provides a method for reducing such coagulation.

8 Claims, 1 Drawing Sheet

(56) References Cited

FOREIGN PATENT DOCUMENTS

| WO | WO-2009/072884 A1 | 6/2009 |
|---|---|---|
| WO | WO-2010/126353 A1 | 11/2010 |
| WO | WO-2010/126362 A1 | 11/2010 |
| WO | WO-2011/093693 A1 | 8/2011 |

OTHER PUBLICATIONS

Beaufrere, et al. "The 'Fast' and 'Slow' Protein Concept", Nestle Nutrition Workshop Series Clinical & Performance Program, 2000, vol. 3, pp. 121-133.

Calbet, et al. "Gastric emptying, gastric secretion and enterogastrone response after administration of milk proteins or their peptide hydrolysates in humans", Eur. J. Nutr., 2004, vol. 43, pp. 127-139.

Caugant, et al. "In Vivo and in Vitro Gastric Emptying of Milk Replacers Containing Soybean Proteins", Journal of Dairy Science, 1994, vol. 77, No. 2, pp. 533-540.

Chavan, et al. "Functional properties of protein isolates from beach pea (*Lathyrus maritimus L.*)", Food Chemistry, 2001, vol. 74, pgs. 177-187.

Decuypere, et al. "Influence of the Partial Replacement of Milk Protein by Soybean Protein Isolates with Different Physical Properties on the Performance and Nitrogen Digestibility of Early-Weaned Pigs", Journal of Animal Science, 1981, vol. 53, pp. 1011-1018.

Fried, et al. "Decrease in gastric emptying time and episodes of regurgitation in children with spastic quadriplegia fed a whey-based formula", The Journal of Pediatrics, Apr. 1992, vol. 120, No. 4, pp. 569-572.

Gorrill, et al. "Body Weight Changes, Pancreas Size and Enzyme Activity, and Proteolytic Enzyem Activity and Protein Digestion in Intestinal Contents from Calves Fed Soybean and Milk Protein Diets", The Journal of Nutrition, 1967, vol. 92, pp. 215-223.

Hoffman, et al. "Protein—Which is Best?", Journal of Sports Science and Medicine, 2004, vol. 3, pp. 118-130.

Mahe, et al. "Gastrojejunal kinetics and the digestion of [15N]beta-lactoglobulin and casein in humans: the influence of the nature and quantity of the protein", The American Journal of Clinical Nutrition, 1996, vol. 63, pgs. 546-52.

Souci, et al. "Food Composition and Nutrition Tables", Wissenschaftliche Verlagsgesellschaft mbH, Auflage 7, 2008.

Westphal, et al. "Postprandial lipid and carbohydrate responses after the ingestion of a casein enriched mixed meal", The American Journal of Clinical Nutrition, 2004, vol. 80, pp. 284-290.

Yvon, et al. "In Vitro Simulation of Gastric Digestion of Milk Proteins: Comparison between in Vitro and in Vivo Data", J. Agric. Food Chem, 1992, vol. 40, pgs. 239-244.

\* cited by examiner

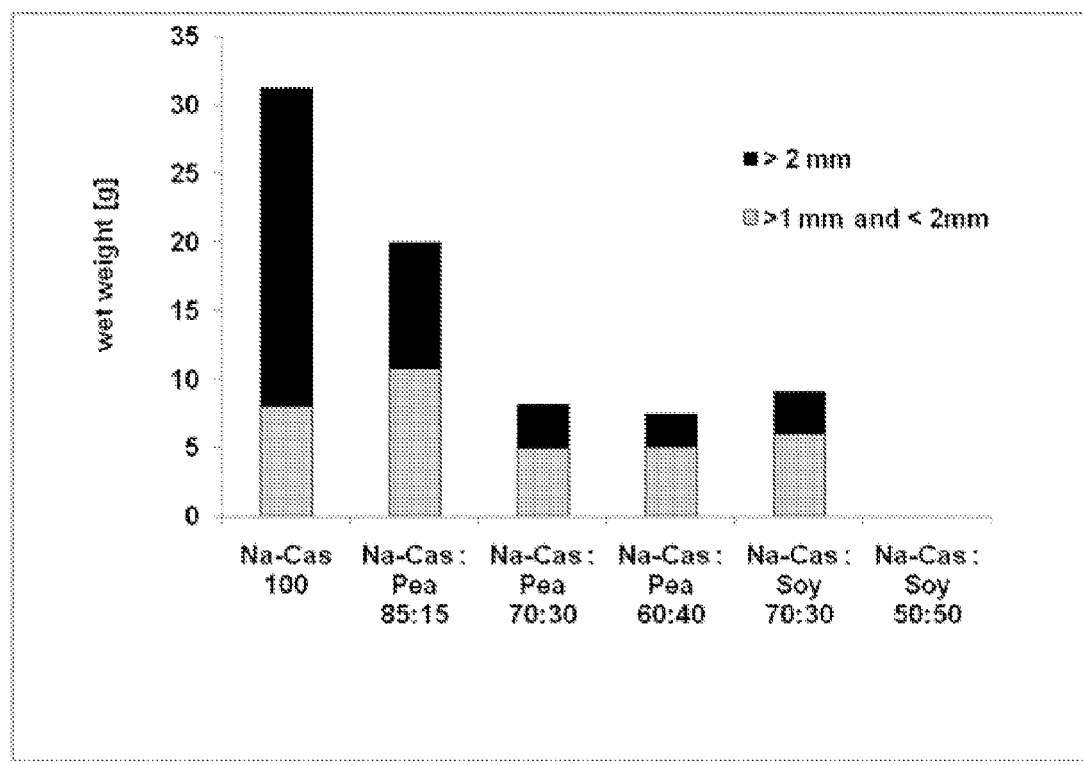

METHOD FOR CONTROLLING THE DIGESTIVE COAGULATION OF PROTEINS

FIELD OF THE INVENTION

This invention is in the field of protein containing nutritional compositions. In particular this invention concerns the coagulation of such compositions in the upper gastro-intestinal tract, more in particular in the stomach. This invention aims to control the digestive coagulation of proteins and preferably aims to reduce the digestive coagulation of proteins.

BACKGROUND OF THE INVENTION

Coagulation of proteins in the upper gastro-intestinal tract, in particular in the stomach is hypothesized to delay gastric emptying. This can result in upper gastrointestinal complications like reflux, gastrointestinal discomfort, and aspiration pneumonia. In particular nutritional compositions mainly containing or consisting of casein and/or caseinate tend to coagulate under conditions in the stomach.

In cases where it is advantageous for subjects to receive easily digestible nutrition it is desired to administer such a nutrition that does not result in too much coagulation of proteins in the stomach. Controlling digestive coagulation of proteins is preferably established for those subjects wherein it is desired to prevent or reduce upper gastrointestinal conditions or complications such as, e.g. intestinal discomfort, reflux, aspiration pneumonia, high gastric residual volume (GRV), vomiting, nausea, bloating, and delayed gastric emptying, or to make it easily digestible in order to promote digestive comfort, reduce gastrointestinal cramping or colics.

Nutritional compositions containing casein, in particular sodium caseinate and vegetable proteins such as soy and/or pea protein are known.

For example US 2003/0104033 teaches enteral formulations comprising 40-95 weight % of caseinate and 5-60 weight % of a stabilizing protein, selected from the group of whey and a one or more vegetable proteins, selected from the group of soy, corn, potato, rice and pea, the most preferred vegetable protein being soy protein. The document is concerned with the reduction of creaming in enteral formulae and is silent with respect to coagulation properties of the composition.

Another example is EP 1 972 346 which discloses a pea-based protein mixture comprising 50 weight % caseinate, 25 weight % milk serum proteins and 25 weight % pea protein. The document is silent with respect to coagulation properties of the composition.

SUMMARY OF THE INVENTION

The present inventors found that a protein composition that under normal conditions coagulates in the stomach, can be made to coagulate to a far lesser extent or not at all, by including a different protein or a protein in a different form resulting in an anti-coagulating effect. For example coagulation of a protein that under normal conditions coagulates in the stomach can be made to coagulate to a far lesser extent or not at all, by including a protein that under the same normal conditions does not coagulate in the stomach. The reduction in coagulation was much more than was expected based on the amount of non-coagulating protein that was included. Hence a synergistic effect on the reduction of coagulation was observed. It is thus considered that the present invention provides an anti-coagulation effect.

The invention will now be further elucidated by describing a number of embodiments of the present invention.

DETAILED DESCRIPTION OF THE INVENTION

The present invention thus concerns a method of preventing or reducing coagulation in the upper gastro-intestinal tract of a subject of coagulating protein present in a nutritional composition, said method comprising further including anti-coagulating protein in said nutritional composition. Preferably the method further comprises the step of administering said nutritional composition to said subject. Preferably the reducing or preventing of coagulation is in the stomach of said subject.

Although the present method is considered not to involve a therapeutic treatment of the animal or human body, it can be recognized that a certain category of ill and/or malnourished and/or hospitalized subjects may benefit from the present invention. In view of this, the invention can also be worded as the use of anti-coagulating protein in the manufacture of a nutritional composition that further comprises coagulating protein, for use in preventing or reducing coagulation in the upper gastro-intestinal tract of a subject of said coagulating protein in said nutritional composition. Preferably the reducing or preventing of coagulation is in the stomach of said subject.

In general coagulation means destabilization or aggregation of proteins by decreasing their electric charge to that of the isoelectric point under the influence of acid and/or enzymes so that protein precipitates are formed. In the context of this invention a protein coagulates if in a stomach digestion model starting with a 6% (w/v) solution of protein in the presence of artificial digestive juice as defined in example 1 after 100 minutes at 37° C. at least 20 wt %, preferably at least 25 wt. %, preferably at least 30 wt. %, preferably at least 35 wt. %, preferably at least 40 wt. % of the protein is present in particles with a diameter of 1 mm or more, preferably at least 10 wt %, preferably at least 15 wt. %, preferably at least 20 wt. %, preferably at least 25 wt. %, preferably at least 30 wt. % of the protein is present in particles with a diameter of 2 mm or more, Suitably a sieve is used to fractionate a gastric digest with respect to particle diameter size.

Anti-coagulation means that a protein has the effect of reducing the coagulation of the coagulating protein with which it is combined. The reducing effect on coagulation is preferably determined in the stomach digestion model starting with a 6% (w/v) solution of combined coagulating protein and anti-coagulating protein in the presence of artificial digestive juice as defined in example 1 after 100 minutes at 37° C. In the context of this invention reducing coagulation means reducing the wt % protein that is present in particles with a diameter of 1 mm or more is reduced by at least 20% compared to the wt % protein that is present in particles with a diameter of 1 mm or more in the absence of anti-coagulating protein under the same conditions.

A specific type of anti-coagulating protein is non-coagulating protein, which is a protein that does not coagulate in the stomach of a human person under normal digestive conditions. In the context of this invention, this means that no particles with a diameter 2 mm or more containing said protein are formed in a stomach digestion model starting with a 6% (w/v) solution of said protein in the presence of artificial digestive juice as defined in example 1 after 100 minutes at 37° C. Preferably a non-coagulating protein is a protein of which no particles with a diameter 1 mm or more are formed.

Coagulating proteins that are suitable for nutritional compositions are known to the skilled person. In the context of the present invention, the coagulating protein preferably is dairy or milk protein, more preferably casein or caseinate, more preferably one or more selected from the group consisting of micellar casein, sodium caseinate, calcium caseinate, potassium caseinate and magnesium caseinate.

Anti-coagulating proteins are preferably selected such so as to provide an amino acid profile commensurate to the nutritional requirements of humans. In particular the anti-coagulating protein is selected to comply with the WHO amino acid profile recommendations for complete nutrition (see: WHO technical report series no. 935—Protein and amino acid requirements in human nutrition: report of a joint FAO/WHO/UNU expert consultation, 2007). Anti-coagulating proteins for example are selected from non-dairy proteins, preferably from vegetable and/or fungal proteins and combinations thereof. Suitable proteins are for example selected from plants such as from rice and wheat, legumes, including beans, lentils, pea and soy, and fungi such as mushrooms or yeast. In the context of this invention "vegetable" relates to protein from plant origin, such as, for instance originating from vegetables such as carrot, pea, chickpea, green pea, cowpea, field pea, kidney bean, lupine, rice, soy, canola, hemp, zein, maize, corn, barley, flax, linseed, and wheat. Equivalent wording may be used, such as "vegetal", "leguminous" or "plant-derived".

Preferably the anti-coagulating protein is selected from pea and soy or a combination thereof.

It is also envisaged that hydrolysed dairy or milk protein, in particular hydrolysed casein can act as an anti-coagulating protein. Thus in one embodiment, the anti-coagulating protein is selected from hydrolysed dairy protein, hydrolysed milk protein, hydrolysed whey protein, hydrolysed casein, hydrolysed caseinate or combinations thereof.

Pea Protein

For the purpose of the present invention, pea protein, preferably intact pea protein, is a suitable anti-coagulating, preferably non-coagulating, protein.

Pea protein is relatively cheap (on the average, pea protein may cost about half the price of caseinates) and as it is added to the nutritional composition it increases the protein content while keeping costs quite low. Pea protein is generally tolerated well by most people, it is lactose-free and is not a common allergen. Pea protein is quite high in cysteine content and can therefore compensate the inadequate amount of cysteine in casein proteins. Furthermore, pea protein is quite high in arginine compared to casein, soy or whey protein which is required for muscle metabolism and which facilitates the intake of body mass while reducing body fat; and it is quite high in lysine, when compared to the vegetable proteins, which is needed to build protein muscle and assist in the maintenance of lean body mass.

Several pea sources are readily available to the skilled person, for example, from Roquette (Lestrem, France) which markets a pea isolate obtained from the yellow pea (*Pisum sativum*), and from Cosucra Groupe Warcoing (Warcoing, Belgium).

Other pea protein sources may originate from green pea, cowpea, chickpea, and field pea.

In one embodiment according to the invention, the pea protein is substantially in intact form or non-hydrolysed.

In another embodiment according to the invention, the pea protein is fermented pea protein or is pea protein hydrolysate.

In the context of this invention, a "non-hydrolysed" protein is equivalent to an "intact" protein, meaning that the protein has not been subjected to an hydrolysis process. However, minor amounts of hydrolysed proteins may be present in the source of non-hydrolysed proteins.

In this context, "minor" should be understood as an amount of about 10 weight % or less. The term "about" should be interpreted as a deviation of plus or minus 10% of the given value.

Soy Protein

For the purpose of the present invention, soy protein, preferably intact soy protein, is a suitable anti-coagulating, preferably non-coagulating, protein.

Soy protein has been used since 1959 as an ingredient for its functional properties in a variety of foods such as salad dressings, soups, vegetarian foods and meat imitations. Its functional properties are emulsification and texturizing. Recently, the popularity of soy protein is increasing, mainly because of its health benefits. It has been proven that soy protein can help to prevent cardiovascular problems and many countries allow health claims for food, which are rich in soy protein. Furthermore, health claims have been made for improving heart health (cholesterol reduction), improving bone health (increased bone density), menopausal symptom relief (reduced hot flashes), performance nutrition (faster muscle recovery) and weight management (satisfying hunger). Soy protein is a vegetable protein that contains the essential amino acids in a relatively high proportion for human health. Soy protein is categorized as a high-quality, complete protein. Soy proteins can be divided into different categories according to their production method. Soy protein isolate (SPI) is the most refined form of soy protein and is mainly used in meat products to improve texture and eating quality. Soy protein isolate contains about 90 percent protein. Soy protein concentrate (SPC) is basically soybean without the water soluble carbohydrates. It contains about 70 percent of protein. Textured soy protein (TSP) is made from soy protein concentrate by giving it some texture. TSP is available as dry flakes or chunks. It will keep its structure when hydrated. Hydrated textured soy protein chunks have a texture similar to ground beef. It can be used as a meat replacement or can be added to meat. Textured soy protein contains about 70 percent protein.

Several soy sources are readily available to the skilled person, for example, from The Solae Company (St. Louis, Mo., USA).

In one embodiment according to the invention, the soy protein is substantially in intact form or non-hydrolysed.

In another embodiment according to the invention, the soy protein is fermented soy protein or is soy protein hydrolysate.

In the context of this invention, a "non-hydrolysed" protein is equivalent to an "intact" protein, meaning that the protein has not been subjected to an hydrolysis process. However, minor amounts of hydrolysed proteins may be present in the source of non-hydrolysed proteins.

In this context, "minor" should be understood as an amount of about 10 weight % or less. The term "about" should be interpreted as a deviation of plus or minus 10% of the given value.

Mixture of Coagulating and Anti-coagulating Protein

The present nutritional composition comprises coagulating protein. Preferably the present nutritional composition comprises at least 25 wt. % coagulating protein based on total protein in the composition. More preferably, the present nutritional composition comprises at least 40 wt. %, preferably at least 50 wt. %, preferably at least 55 wt. %, more preferably at least 60 wt. % or at least 65 wt. % or at least 70 wt. % coagulating protein based on total protein in the composition. Advantageously, the present nutritional composition comprises not more than 99 wt % coagulating protein based on total protein in the composition. More preferably the present nutritional composition comprises not more than 97 wt. %, more preferably not more than 95 wt. % or not more than 90 wt. % or not more than 85 wt. % coagulating protein based on total protein in the composition.

The present nutritional composition comprises anti-coagulating protein. Preferably the present nutritional composition comprises at least 1 wt % anti-coagulating protein based on total protein in the composition. More preferably, the present nutritional composition comprises at least 3 wt. %, more preferably at least 5 wt. % or at least 10 wt. % or at least 15 wt. % anti-coagulating protein based on total protein in the composition. Advantageously, the present nutritional composition comprises not more than 75 wt. % anti-coagulating protein based on total protein in the composition. More preferably the present nutritional composition comprises not more than 60 wt. %, preferably not more than 50 wt. %, preferably not more than 45 wt. %, more preferably not more than 40 wt. % or not more than 35 wt. % or not more than 30 wt. % anti-coagulating protein based on total protein in the composition.

The mixture of coagulating and anti-coagulating protein, or in other words anti-coagulating protein mixture, can be prepared by methods for preparing nutrition composition known per se, for example by mixing the protein ingredients, optionally in the presence of other ingredients normally present in nutritional compositions or such other ingredients may be added after mixing of the protein ingredients.

In one embodiment according to the present invention, the nutritional composition comprises between 25-99 wt. % coagulating protein based on total weight of protein in the composition and between 1-75 wt. % anti-coagulating protein based on total weight of protein in the composition. Preferably the nutritional composition comprises between 40-97 wt. %, preferably between 50-95 wt. %, preferably between 60-90 wt. %, preferably between 70-85 wt. % coagulating protein based on total weight of protein in the composition and between 3-60 wt. %, preferably between 5-50 wt. %, preferably between 10-40 wt. %, preferably between 15-30 wt. % anti-coagulating protein based on total weight of protein in the composition.

Reducing Coagulation

The present method is for reducing coagulation in the stomach of coagulating protein in a nutritional composition and the method involves including anti-coagulating protein in said nutritional composition. In the context of this invention coagulation is reduced if the amount of protein that is present in particles with a diameter of 1 mm or more, is reduced by at least 20% in the stomach digestion model as defined above compared to the amount of protein that is present in particles with a diameter of 1 mm or more of a coagulating protein in the absence of anti-coagulating protein in said stomach digestion model, preferably compared to the amount of protein that is present in particles with a diameter of 1 mm or more of a composition wherein the coagulating protein is the sole protein source. Preferably the amount of protein in particles with a diameter of 1 mm or more is reduced by at least 25%, more preferably by at least 30%, more preferably by at least 40% or by at least 50%, more preferably by at least 60% even more preferably by at least 70%, more preferably by at least 80%, more preferably by at least 90%.

Reducing coagulation in the stomach of coagulating protein is understood to mean that the addition of an anti-coagulating protein or a mix thereof to a coagulating protein or mix thereof yields a synergistic effect on reduction of coagulation beyond what is expected arithmetically.

Applications

Due to a variety of reasons, such as diseases, medical conditions, malnutrition, medical disabilities, post-surgery, etc. patients may not be able to obtain the necessary nutrition by ingesting food through the mouth, e.g. orally, by eating or drinking. Therefore, it has been known to provide medical enteral nutrition by oral nutritional supplements or tube feeding. Tube feeding is given to provide nutrition to patients which cannot obtain nutrition by swallowing, using a device such as a nasogastric feeding tube or a naso jejunal feeding tube, or by using a percutaneous endoscopic gastrostomy (PEG) or PEG—jejuno-feeding system. In the context of this application, the state of being fed by nutritional supplements and/or a by a feeding tube is called enteral feeding, comprising all of the abovementioned tube feeding systems, and the nutrition used in the feeding by nutritional supplements and/or a by a feeding tube is called enteral nutrition. Use of such enteral nutrition may be temporary for the treatment of acute conditions, or lifelong in the case of chronic disabilities. In the latter case, it is primordial that the enteral nutrition is designed for long-term administration containing all necessary components. In particular, the enteral nutrition contains a protein fraction which at least meets and preferably exceeds the WHO amino acid profile recommendations for complete nutrition. With advances in medicine resulting in increased life expectancy and better disease treatment, a large number of patients would benefit from such enteral nutrition designed to provide long-term enteral nutrition. Furthermore, said enteral nutrition should be easily digestible and not lead to upper gastrointestinal conditions or complications such as, e.g. intestinal discomfort, reflux, aspiration pneumonia, high gastric residual volume (GRV), vomiting, nausea, bloating, and delayed gastric emptying. Coagulation of proteins in the stomach is hypothesized to delay gastric emptying, This will result in upper gastrointestinal complications such as, e.g. intestinal discomfort, aspiration pneumonia, high gastric residual volume (GRV), vomiting, nausea, bloating, and delayed gastric emptying, especially in vulnerable persons, such as hospitalized patients. Hence, the present method is for providing nutrition. In one embodiment, the present method is for prevention or treatment of upper gastrointestinal complications such as, e.g. intestinal discomfort, aspiration pneumonia, high gastric residual volume (GRV), vomiting, nausea, bloating, and delayed gastric emptying. The present method preferably involves administering the nutritional composition to humans, preferably to humans that benefit from receiving easily digestible nutrition, preferably to humans with digestive tract complications, preferably to humans with digestive problems, preferably to hospitalized patients, preferably to a person that is in a disease state, a person that is recovering from a disease state, a person that is malnourished, a baby, an infant and/or a toddler. The present method preferably involves administering the nutritional composition orally, by eating or drinking, preferably enterally by tube feeding.

In one embodiment the invention concerns the use of anti-coagulating protein in the manufacture of a nutritional composition that further comprises coagulating protein, for the reduction of upper gastrointestinal conditions or complications selected from the group of reflux, aspiration pneumonia, high gastric residual volume (GRV), vomiting, nausea, bloating, and delayed gastric emptying.

In one embodiment the invention concerns the use of pea protein or soy protein or both in the manufacture of a nutritional composition that further comprises caseinate, for, use in preventing or reducing coagulation in the stomach of said caseinate.

In one embodiment the invention concerns the use of pea protein or soy protein or both in the manufacture of a nutritional composition that further comprises caseinate, for the reduction of upper gastrointestinal conditions or complications selected from the group of reflux, aspiration pneumonia, high gastric residual volume (GRV), vomiting, nausea, bloating, and delayed gastric emptying.

Another category of subjects that can benefit from the present method are infants. Thus in one embodiment according to the present invention the nutritional composition is an infant formula, a follow-on formula and/or a toddler formula. In one embodiment according to the present invention the nutritional composition is in a suitable form for administration to a baby, an infant and/or a toddler.

In one embodiment according to the present invention the nutritional composition is to promote digestive comfort, reduce gastrointestinal cramping and/or reduce colics.

Also athletes and sportsmen and sportwomen can benefit from the present method. Thus in one embodiment according to the present invention the nutritional composition is a drink or a sportsdrink or a spoonable composition or a solid or a bar.

Also the present method can be of benefit in weight management of a subject. In one embodiment according to the present invention the nutritional composition is for use in weight management. Preferably the nutritional composition is a spoonable product.

Dosage Unit

The nutritional composition according to the invention preferably has the form of a complete food, i.e. it can meet all nutritional needs of the user. As such, the liquid enteral nutritional composition according to the invention preferably contains 1000 to 2500 kcal per daily dosage. Depending on the condition of the patient, a daily dose is about 25 to 35 kcal/kg bodyweight/day. Therefore, a typical daily dose for a 70 kg person contains about 2000 kcal. The complete food can be in the form of multiple dosage units, e.g. from 8 (250 ml/unit) to 2 units (1 l/unit) per day for an energy supply of 2000 kcal/day using a liquid enteral nutritional composition according to the invention of 1.0 kcal/ml. Preferably, the nutritional composition is adapted for tube feeding.

In the case the liquid enteral nutritional composition is an oral food supplement, it can for example to be used in addition to a non-medical food or normal diet. Preferably, as an oral supplement, the liquid enteral nutritional composition contains per daily dosage less than 1500 kcal, in particular as a supplement, the nutritional composition contains 500 to 1000 kcal per daily dose. The food supplement can be in the form of multiple dosage units, e.g. from 2 (250 ml/unit) to 10 units (50 ml/unit) per day for an energy supply of 500 kcal/day using a liquid enteral nutritional composition according to the invention of 1.0 kcal/ml.

Preferably, the nutritional composition is packaged, stored and provided in a container such as plastic bag or a pouch or the like. A variety of such containers is known, for example 500 ml, 1000 ml, and 1500 ml containers are known in the art. It should be noted that any suitable container can be used to package, store and provide the nutritional composition according to the invention.

In one embodiment of the present invention, the nutritional composition is provided in a ready to use liquid form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

The invention will now be further elucidated by several examples, without being limited thereby.

FIGURE

The FIGURE shows the absolute wet weight of coagulates between 1 mm and 2 mm and bigger than 2 mm after 100 minutes of gastric digestion of different protein mixtures of sodium caseinate (Na-Cas) and pea protein (pea) or soy protein (soy).

EXAMPLES

Example 1

Experimental Study Outline

The coagulation properties upon gastric digestion were investigated for a solution of 100% sodium caseinate and solutions of protein mixtures with representative ratios of sodium-caseinate to pea protein of 85:15, 70:30, and 60:40, and for protein mixtures with representative ratios of sodium-caseinate to soy protein of 70:30, and 50:50 with 6% protein (w/v).

Gastric Digestion

Stomach digestion was mimicked over 100 minutes in a computer controlled substrate pump setup (Multifermentor fed-batch; DASGIP AG, Juelich, Germany) at 37° C. upon continuous stirring.

For each experiment, 150 ml of protein solution were used as the starting volume. Per experiment, a total of 45 ml of artificial stomach juice (50 mM NaCl, 15 mM KCl, 1 mM $CaCl_2.H_2O$, 15 mM $NaHCO_3$, 0.014% (w/v) pepsin (porcine stomach, sigma p7012), 0.019% (w/v) lipase (*Rhizopus oryzae*, DF 15K Amano Pharmaceutical Co, Ltd Nagoya); pH 4.0) was added. The stomach juice was added in two steps with different flow rates. In the first two minutes, a flow rate of 225 ml/h was used. For the rest of the experiment the flow rate was 23 ml/h. In addition, in the first 60 minutes of the experiment a total of 30 ml of artificial saliva (0.1 M NaCl, 30 mM KCl, 2 mM $CaCl_2.2H_2O$, 15 mM $NaHCO_3$, 0.065% (w/v) α-amylase (Sigma A 6211); pH 6.3) was added continuously to the solution.

The pH was decreased over 100 minutes from a pH of 6.6 at start to a final pH of 2.0 (pH at start=6.6, pH at 8 minutes=5.0, at 15 minutes=4.0, at 42 minutes=3.0, at 100 minutes=2.0) by the addition of 1 M HCl upon continuous mixing. If necessary, acidification was automatically corrected by the addition of an alkaline solution (1 M $NaHCO_3$, 3 M NaOH).

Determination of Coagulate

After gastric digestion, the samples were poured over metal sieves to yield fractions with particle sizes of a) bigger than 2 mm, b) below 2 mm and above 1 mm, c) below 1 mm and above 0.25 mm and d) below the limit of 0.25 mm. In short, the wet weight fractions were determined by weighing each individual sieve with the coagulate on it and subtracting the weight of each sieve.

Results

After 100 minutes of stomach digestion, sodium-caseinate yields the highest amount of coagulate. Addition of either pea or soy diminishes this amount. As such, addition of 15% (w/w) pea protein to the sodium-caseinate diminishes coagula bigger than 2 mm by more than 60% and addition of 40% pea protein diminishes caseinate coagula by more than 90%.

It should be understood that various changes and modifications to the presently preferred embodiments described herein will be apparent to those skilled in the art. Such changes and modifications may be made without departing from the spirit and scope of the invention and without diminishing its advantages. It is therefore intended that such changes and modifications are covered by the appended claims.

The invention claimed is:

1. A method of providing nutrition to a human subject in need of tube feeding, the method comprising administering to the subject by tube feed a nutritional composition comprising:
   (a) 70-85 wt % coagulating protein; and
   (b) 15-30 wt % non-coagulating protein consisting of pea protein and/or soy protein wherein the non-coagulating protein prevents or reduces the coagulation of the coagulating protein in the upper gastro-intestinal tract.

2. The method according to claim 1, wherein the coagulating protein comprises dairy protein.

3. The method according to claim 1, wherein the coagulating protein comprises caseinate.

4. The method according to claim 1, wherein the non-coagulating pea or soy protein is hydrolyzed.

5. The method according to claim 1, wherein the subject suffers from digestive tract complications.

6. The method according to claim 5, wherein the subject is an infant or a toddler.

7. The method according to claim 1, wherein the subject suffers from upper gastrointestinal conditions or complications selected from the group consisting of reflux, aspiration pneumonia, high gastric residual volume (GRV), vomiting, nausea, bloating, gastrointestinal cramping, colics, and delayed gastric emptying.

8. The method according to claim 1, wherein the non-coagulating protein consists of pea protein.

* * * * *